United States Patent [19]
Griesmer et al.

[11] Patent Number: 5,379,335
[45] Date of Patent: Jan. 3, 1995

[54] AUTOMATIC GRID OSCILLATION CONTROL FOR RADIOGRAPHIC IMAGING SYSTEMS

[75] Inventors: Jerome J. Griesmer, Kirtland; Lynn W. Krebs, Aurora, both of Ohio

[73] Assignee: Picker International, Inc., Cleveland, Ohio

[21] Appl. No.: 103,600

[22] Filed: Aug. 9, 1993

[51] Int. Cl.⁶ .............................................. G21K 1/00
[52] U.S. Cl. ................................. 378/155; 378/154
[58] Field of Search ................................. 378/154, 155

[56] References Cited

U.S. PATENT DOCUMENTS

| | | |
|---|---|---|
| 2,486,089 | 10/1949 | Zavales .............................. 378/155 |
| 2,767,323 | 10/1956 | Stava et al. . | 
| 4,380,086 | 4/1983 | Vagi . |
| 4,803,716 | 2/1989 | Ammann et al. .................... 378/155 |

Primary Examiner—Craig E. Church
Attorney, Agent, or Firm—Timothy B. Gurin; Randall A. Notzen

[57] ABSTRACT

A radiographic imaging system is comprised of a radiation source 12, a radiation adsorbing grid assembly 18, an image producing element 22 a controller 34, an exposure sequence start means 28 and a grid assembly oscillation means 20. The radiation source and grid define a subject receiving gap, wherein an object under examination is disposed, and through which the source propagates a beam of radiation onto the face of the image producing element. The controller recognizes when the exposure sequence start means is activated and starts the exposure sequence. The exposure sequence is comprised of an exposure preparation interval and an exposure interval. The exposure preparation interval is comprised of a radiation source preparation time and a point-in-time when the grid assembly oscillation commences oscillating the grid assembly. The point-in-time when the grid assembly oscillation commences occurs relative to the start of the exposure preparation interval to minimize the formation of gird lines on the image producing element.

20 Claims, 5 Drawing Sheets

AUTOMATIC GRID OSCILLATION CONTROL FOR RADIOGRAPHIC IMAGING SYSTEMS

BACKGROUND ART

Systems that produce a radiographic image by passing a beam of penetrative radiation through a subject and impinging the radiation beam on an image-producing element, such as a film disposed in a scintillating film cassette, generally employ one or more radiation absorbing grid assemblies interposed between the subject and the element. The grid assemblies reduce clouding of the film image caused by scattered radiation. If, however, the grid assemblies are stationary during radiation exposure the radiation absorbing characteristics of the grid cause an image of the grid strips, i.e. grid lines, to form on the film.

Various approaches have been devised to minimize the appearance of grid lines. One approach was to sinusoidally oscillate the grid between two endpoints such that the grid was moving during an appreciable period of the exposure to blur the grid lines. Another approach is disclosed in U.S. Pat. No. 2,767,323 to Stava et al. which suggests a motor and cam combination to oscillate the grid assembly such that the grid velocity is relatively constant during a majority of the grid oscillation and accelerates quickly through an endpoint thereby minimizing the time the grid remains stationary at the endpoint. Thus in the Stava patent the motion of the grid assembly over time is not sinusoidal but more of a triangular shaped waveform. Still another approach to minimize grid lines is disclosed in U.S. Pat. No. 4,380,086 to Vagi which suggests altering the displacement of the grid assembly motion endpoints during successive oscillations such that the positions of the stationary point of the grid motion at an endpoint is not repeated during a single exposure.

All of these approaches achieve a reduction in the appearance of grid lines for exposures of approximately 0.5 seconds or longer in duration. However, as exposure times become progressively shorter, for example 0.05 seconds, the independent functions of grid motion and exposure time occasionally coincide such that the grid is at or near zero velocity at an endpoint during exposure thereby resulting in random grid lines appearing on the film. The Stava Patent, referenced above, suggests overcoming this problem by fixing the exposure start to grid motion during an exposure sequence. A motor/cam arrangement is proposed which, after an exposure sequence is initiated, commences grid motion. A fixed period of time later, the exposure is initiated. In this fashion, the exposure occurs during the substantially constant velocity portion of the grid motion. One drawback to the Stava invention is that the cams and switches must be mechanically adjusted to change the exposure duration or the relationship of the exposure start to the grid motion. Another drawback is that the Stava invention cannot be dynamically adjusted to account for imaging system events that occur prior to the actual exposure, such as the x-ray tube rotor start-up and the x-ray tube filament preheat. Still another drawback is that for exposure durations greater than the time required for one revolution of the cam, the exposure start switch must be manually maintained in the closed position to complete the exposure.

As radiographic imaging technology has progressed, one feature that evolved is the ability to take a plurality of relatively short duration rapidly sequenced exposures on different portions of a single sheet of film by sequentially moving the film cassette from one image position to another. When utilized in conjunction with a system that takes a series of rapidly sequenced exposures the prior art oscillation approaches of reducing the appearance of grid lines exhibit the same problems previously discussed. In addition to the previously mentioned drawbacks, the Stava invention does not provide an apparatus for performing a series of rapidly sequenced exposures on separate subsections of the image producing element while ensuring that the grid is not stationary during an appreciable portion of each exposure.

It is the object of this invention to overcome these problems and others by providing a new and improved apparatus and method to minimize the formation of grid lines for a single exposure of a sheet of film or a sequential series of exposures of separate subsections of a sheet of film.

SUMMARY OF THE INVENTION

In accordance with one embodiment of the present invention a radiographic imaging system is provided. In the system, a source of penetrative radiation for propagating a radiation beam along a path is provided. An image producing element is positioned in the beam path for receiving the radiation beam. A grid assembly is positioned in the beam path between the radiation source and the image producing element. The grid assembly includes a radiation absorbing grid strip. A grid assembly oscillation means for oscillating the grid assembly transverse to the beam path is also provided. A controller is operatively connected to the radiation source and the grid assembly oscillation means for controlling the start of radiation production and the start of the grid oscillation. An operator interface is connected to the controller for receiving operator input of exposure parameters and for communicating the same to the controller. An exposure sequence start means is connected to the controller for signaling to the controller the start of a first exposure sequence. The first exposure sequence is comprised of an exposure preparation time interval and an exposure interval. The exposure preparation time interval is comprised of a radiation source preparation time interval and grid oscillation start point. One of the grid oscillation start point and the start of the exposure interval is functionally related to the input technique factors and variable as a function thereof relative to the start of the first exposure sequence.

In accordance with one aspect of the present invention the radiation source preparation time interval is comprised of an interval of time sufficient for the filament of the radiation source to be heated by an electrical current to the point that electrons are boiled off and an anode of the radiation source is accelerated from an at rest position to a constant angular velocity.

In accordance with a another aspect of the invention a lookup table is provided for storing data values comprised of at least one of a first time value and a second time value. The first time value corresponds to the time between the start of the exposure preparation interval and the start of the grid oscillation. The second time value corresponds to the time between the start of the exposure preparation interval and the start of the radiation exposure.

In accordance with yet another aspect of the invention the lookup table values are selectively retrieved by the controller in response to operator input of exposure parameters. The controller operates the imaging system in response to at least one of the operator input exposure parameters and the retrieved data values.

In accordance with still another aspect of the invention the grid oscillation start point occurs at one of the radiation source preparation time interval and at the end of the radiation source preparation time interval.

In accordance with yet another aspect of the invention a cassette movement means is provided for selectively positioning subsections of the film cassette in the radiation beam path in response to signals from the controller.

In accordance with still another aspect of the invention the controller synchronizes the movement of the cassette and the activation of the radiation source to produce a second exposure sequence on a select subsection of the image producing element. The second exposure sequence is comprised of an exposure preparation interval and an exposure interval. During the second exposure preparation interval the cassette advances to a second exposure position and the grid assembly advances to a motion end point and commences oscillation therefrom. At the end of the exposure preparation interval the controller starts the exposure interval.

In accordance with another aspect of the invention the imaging system includes an Automatic Exposure Control (AEC) means. The AEC means is at least partially disposed in the radiation beam path for sensing the radiation in the beam path and for signaling at least one of the radiation source and the controller when a predetermined amount of radiation has been received the the AEC means.

In accordance with another aspect of the invention the cassette advances to a second exposure position, the grid advances to a grid motion end point and commences oscillation therefrom. The radiation source commences producing radiation for a second exposure interval shortly after the commencement of the grid oscillation.

In accordance with another aspect of the invention a cassette position sensor is operatively connected to the cassette and controller for indicating when the cassette has arrived at an exposure position.

In accordance with another aspect of the invention a grid position sensor is operatively connected to the grid assembly and the controller for indicating to the controller that the grid assembly has arrived at an end point of motion travel.

In accordance with another embodiment of the present invention an apparatus for controlling an exposure sequence of a radiographic imaging system is provided. The apparatus is comprised of a controller and an operatively connected operator interface terminal. The operator interface terminal receives operator input of technique factors and communicates said input to the controller. The controller commences at least one of the oscillation of a radiation absorbing grid assembly from a grid motion end point and radiation production from a radiation source as a function of said input technique factors relative to the start of the first exposure sequence.

In accordance with another aspect of the invention a method of controlling the movement of a grid assembly in a diagnostic imaging system during an exposure sequence is provided. The method is comprised of the steps of positioning the grid assembly and at least a portion of an Image producing element in a radiation beam path produced by the diagnostic imaging system.

Entering technique factors into an operator interface terminal. Activating an exposure sequence start means. Preparing a radiation source to produce the radiation beam. Accelerating the grid assembly from an at rest position to a substantially constant velocity. Causing the radiation source to produce radiation along the beam path. Exposing at least a portion of the image producing element to the radiation beam. And terminating the radiation produced by the radiation source. In the method the commencement of at least one of the accelerating step is functionally related to the input technique factors and variable as a function thereof relative to the start of the exposure sequence.

In accordance with another aspect of the invention the method is comprised of the further steps of, moving an unexposed portion of the image producing element into the beam path. Accelerating the grid assembly from an at rest position to a substantially constant velocity. Causing the radiation source to produce radiation along the beam path. Exposing the unexposed portion of the image producing element in the beam path to the radiation beam. Terminating the radiation produced by the radiation source. Setting the grid adjacent a grid motion end point. And, repeating the above steps until all select subsections of the image producing element are exposed.

An advantage of the present invention is that for single or multiple exposure sequences the system operation is synchronized to minimize the formation of grid lines on the image producing element.

Another advantage of the invention is that the operation of the system is functionally related to the entry of exposure technique factors.

Still other advantages will become apparent upon reading and understanding the following detailed description.

DETAILED DESCRIPTION OF THE PREFERRED EMBODIMENT

Figure 1:
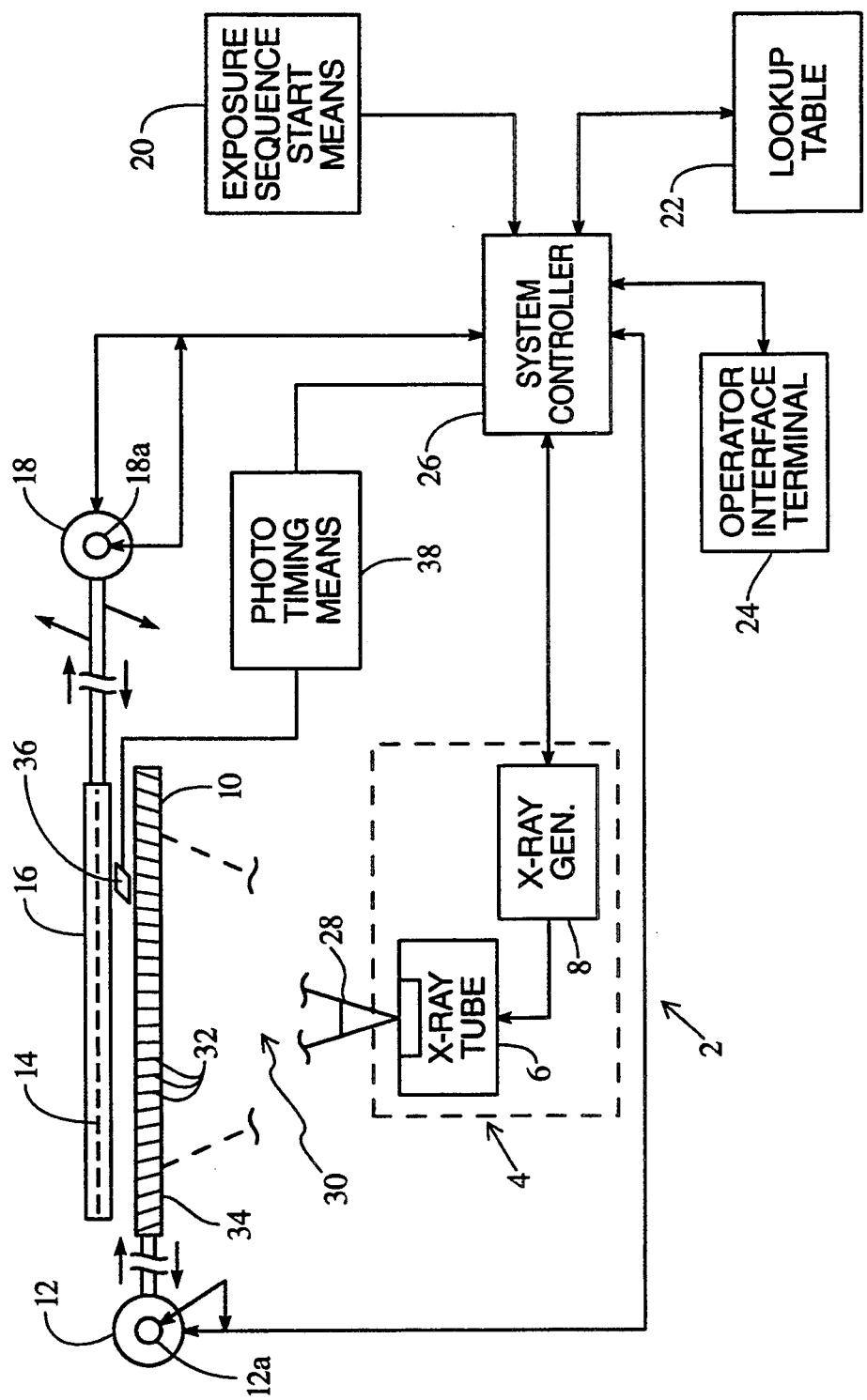
FIG. 1 is a schematic diagram of a portion of a radiation imaging system constructed according to the invention.

With reference to FIG. 1, a penetrative radiation imaging system 2 is comprised of a source of penetrative radiation 4 having an x-ray tube 6 and x-ray generator 8, a radiation absorbing grid 10, a grid assembly oscillation means 12, a sheet of film 14 disposed in a film cassette 16, a film cassette movement means 18, an exposure sequence start means 20, a memory means such as a LookUp Table (LUT) 22, an operator interface 24 and a controller 26. The controller 26 is operatively connected to the generator 8, the grid oscillation means 12, the film cassette movement means 18, the operator interface 24, the exposure sequence start means 20 and the LUT 22.

When activated by controller 26 the radiation source 4 directs a beam of radiation 28 sequentially through an examination gap 30, in which an object under examination (not shown) is disposed, through the grid 10, through a face of the film cassette 16 and onto the face of the film sheet 14 where a radiographic image of the object is produced. The grid 10, film cassette 16 and film 14 are disposed generally orthogonal to the central portion of the radiation beam.

The grid 10 is comprised of a plurality of thin lead strips 32 which are supported on edge by a suitable housing 34 and typically aligned in a radial pattern extending through the radiation beam focal spot. The grid assembly oscillation means 12 supports the grid assembly 10 for oscillation between two endpoints.

The x-ray tube 6 is comprised of a source of electrons and an annular anode disposed in an evacuated envelope. The source of electrons is typically a filament disposed in a cathode assembly. Prior to use the filament is heated by electrical current to the point that electrons are boiled-off the filament. Once the filament is at a temperature sufficient to boil-off electrons an electrical potential is applied between the anode and cathode to accelerate the boiled-off electrons to the anode. The anode is comprised of a material that emits x-radiation in response to the interaction of the accelerated electrons striking the anode surface. The interaction of the electrons and the anode creates a significant amount of localized heating. If this heating were to continue unabated the anode material would melt at that spot thereby affecting the ability of the tube to produce radiation. To overcome this localized heating problem the anode is rotated such that the anode face constantly rotates through the electron beam. The anode rotation provides sufficient time for the localized portion of the anode to dissipate the heat caused by the interaction of the electron beam and the anode between subsequent exposures of the anode spot to the electron beam.

The film cassette movement means 18 provides for select positioning of the film cassette 16 between a film cassette loading and unloading position and to any number of other select positions within the radiation beam path for exposure of either an entire sheet of film or select subsections of a single sheet of film.

The exposure sequence start means 20, in response to an operator activation thereof, provides an signal to the controller to commence an exposure sequence.

The operator interface 24 accepts operator input of exposure parameters, as are known in the art, and communicates the same to the controller 26. Exposure parameters may include, but are not limited to, such parameters as x-ray tube current (mA), x-ray tube voltage (kV), the number of exposures to be created on a single sheet of film and the exposure duration. The LUT 22 Is a memory device with stores a plurality of $t_1$ and $t_2$ time-interval values corresponding to the various embodiments and/or operating modes of the system as more fully described below. The $t_1$ and $t_2$ time intervals are selectively addressed by the controller in response to the operator entering different exposure parameters and/or the selection of a single exposure or exposure sequence series into the operator interface. The entered exposure parameters and addressed time intervals are used by the controller to synchronize the system operation as described below.

In an extension of the embodiment illustrated in FIG. 1, an automatic exposure control (AEC) means is provided. The AEC means is comprised of a radiation sensor and a photo-timing means 38. The radiation sensor 36 is disposed in the beam path 28 and operatively connected to a photo-timing means 38. The photo-timing means 38 is operatively connected to the controller 26. The radiation sensor senses the radiation impinging thereon and transmits an signal representative thereof to the photo-timing means. When the photo-timing means determines that a predetermined amount of radiation has been received by the radiation detector the photo-timing means signals the controller to terminate the radiation exposure. Upon receiving the photo-timing means signal, the controller signals the generator to terminate the exposure.

In accordance with the present invention each exposure sequence is comprised of an exposure preparation interval and an exposure interval. The exposure preparation interval is comprised of an interval of time sufficiently long to prepare the x-ray tube to make an exposure, advance the film cassette into position and to accelerate the grid assembly to a substantially constant velocity. The exposure interval is the interval during which the radiation source produces the beam of radiation for a radiographic procedure.

The following equations define a set of general conditions that are applicable to various exposure preparation interval(s) of the present invention:

$$t_1 = t_{0\ grid\ acceleration} - t_{0\ exposure\ sequence} \quad \text{Equation (1)}$$

$$t_2 = t_{0\ exposure\ interval} - t_{0\ exposure\ sequence} \quad \text{Equation (2)}$$

$t_{0\ exposure\ sequence}$ = The point in-time that an exposure sequence begins.

$t_{0\ grid\ acceleration}$ = The point in-time during an exposure sequence that the grid acceleration begins.

$t_{0\ exposure\ interval}$ = The point in-time during an exposure sequence that the exposure interval begins i.e.; when the radiation beam is turned on.

The selected values of $t_1$ and $t_2$ vary, in accordance with the selection of the various embodiments of the present invention or whether the exposure sequence is the first or subsequent exposure sequence in an exposure sequence series.

With reference to FIGS. 2, 3(a)-(c) and continuing reference to FIG. 1, in a first embodiment, the exposure preparation interval 43(a), (b) or (c) is comprised of a radiation source preparation time interval 46 followed by the start of the grid acceleration ($t_{0\ grid\ acceleration}$) at point 54. An exposure interval 50(a), (b) or (c) immediately follows the end of the exposure preparation interval 43(a), (b) or (c). The exposure preparation interval ends after sufficient time has passed to result in the tube being prepared to make an exposure, the film cassette has advanced into position and the grid has accelerated to a substantially constant velocity. In this embodiment, $t_1$ in Equation 1 is equal to interval 46 and $t_2$ in Equation 2 is equal to interval 43(a), (b) or (c). The radiation source preparation time interval 46 commences at point 52 (i.e. $t_{0\ exposure\ sequence}$) upon activation of the exposure sequence start means 28. During Interval 46, the x-ray tube filament is heated by electrical current to the point that electrons are boiled-off the filament and the anode is accelerated from an at rest position to a constant angular velocity. Concurrently the film cassette is advanced to an exposure position. The value of $t_1$ is selected to provide sufficient time to prepare the x-ray source for radiation production. When $t_1$ expires the radiation source is prepared and grid acceleration commences at point 54. The grid acceleration starts during the exposure preparation interval 43(a), (b) or (c) immediately following the expiration of $t_1$. The value of $t_2$ is selected to provide sufficient time to accelerate the grid from an at rest position at one of its motion end points 44, 45 to a substantially constant velocity. When $t_2$ expires the grid has accelerated to a substantially constant velocity and an exposure can commence. The duration of exposure Interval 50(a), (b) or (c) is determined by the nature of the exposure parameters selected by the operator at operator Interface 32 and dictates the time between the start of the grid motion and the start of the exposure interval to assure optimum grid motion in relation to exposure time.

The LUT 30 stores a plurality of timing information corresponding to a plurality of $t_1$ and $t_2$ values. The $t_1$ values are determined by theoretical and empirical data relating to the time for the x-ray tube filament to heat to an appropriate discharge temperature and the time for the anode to accelerate to an acceptable angular velocity for a plurality of different exposure durations and exposure rates. The $t_2$ values are determined by theoretical and empirical data relating to the time for a plurality of grids of different sizes and masses to accelerate to a substantially constant velocity between end points. This data is translated into values of $t_1$ and $t_2$ that the controller can address to synchronize the system operation. The $t_1$ and $t_2$ values are loaded into select locations of the LUT for subsequent retrieval by the controller. The controller retrieves appropriate values of $t_1$ and $t_2$ from the LUT in response to the operator entry of exposure parameters. In the above described embodiment the retrieved values of $t_1$ and $t_2$ establishes the duration of intervals 46 and 43(a), (b) or (c) respectively.

From the above it should be appreciated that the selection of various values of $t_1$ and $t_2$ allow for control of the length of the source preparation time interval, the point in time when the grid acceleration commences and the point-in-time when the exposure interval commences.

Figure 2:
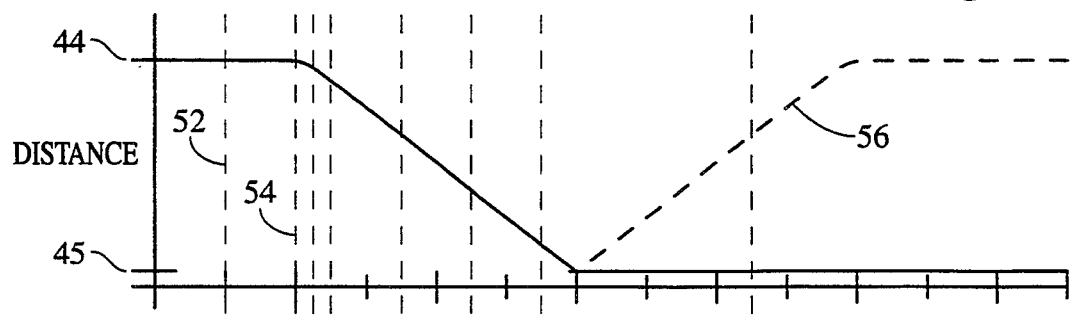
FIG. 2 is a graphical Illustration of grid position versus time for a single exposure according to a preferred embodiment of the invention.
Figure 3:
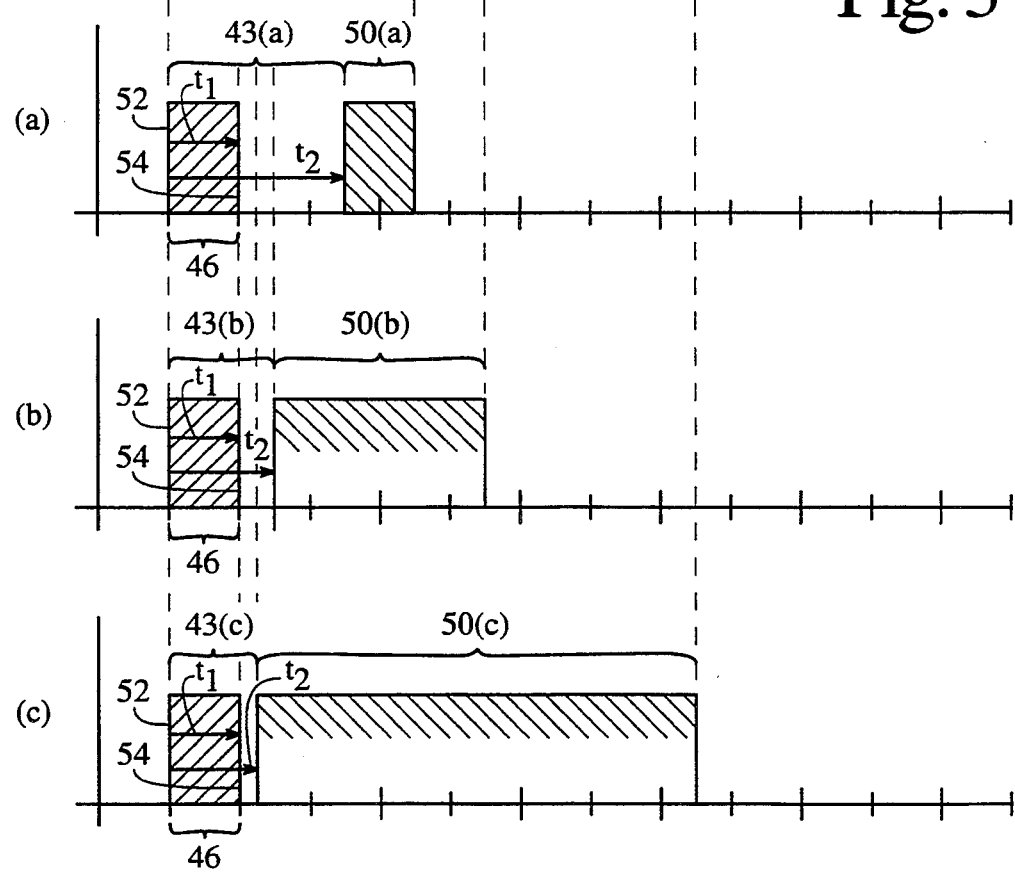
FIGS. 3(a)–(c) illustrates various exposure sequence timing relationships relative to the grid position versus time graph of FIG. 2.

Referring to FIGS. 2 and 3(a), one exemplary exposure sequence is shown wherein the exposure interval 50(a) is relatively short. The exposure sequence illustrated in FIG. 3(a) is comprised of an exposure preparation interval 43(a) commencing at point 52 followed by an exposure interval 50(a). The exposure preparation interval 43(a) Is comprised of a source preparation interval 46 commencing at point 52 followed by the start of the grid acceleration at point 54. Specifically, in response to the entry of exposure parameters on the operator interface 32, the controller 34 selects a $t_1$ value which defines interval 46. The controller also selects a $t_2$ value which defines the duration of the exposure preparation interval 43(a). In the example of FIG. 3(a), the exposure preparation interval 43(a) is selected such that the x-ray tube 1s ready to produce radiation prior to starting the grid acceleration at point 54 and the exposure interval 50(a) begins and ends approximately around the midpoint of the grid excursion between end points (44, 45). It is to be appreciated, however, that beginning and ending the exposure interval around the midpoint of the grid excursion is not necessary for the practice of the invention. Upon activation of the exposure sequence start means 28 intervals 43(a) and 46 begin at point 52. After the radiation source preparation interval 46 has expired the controller starts the grid acceleration at point 54. After interval 43(a) the controller starts the exposure interval 50(a). At the expiration of the exposure interval 50(a) the controller terminates the exposure and signals the grid oscillation means 20 to set the grid adjacent a motion end point in preparation for the next exposure sequence. In this example, since the exposure interval Is shorter than the time for the grid to traverse between opposite end points the exposure can occur within the time the grid travels at a substantially constant velocity from one end point to another.

In another example, shown in FIG. 3(b), the exposure interval 50(b) is shorter than the time for the grid to traverse between end points (44, 45) and substantially longer than corresponding exposure interval 50(a) in FIG. 3(a). In this example, the value of $t_2$ is selected which defines source preparation interval 43(b). The duration of interval 43(b) is shorter than the corresponding interval 43(a) in illustration 3(a) to permit the exposure interval 50(b) to begin sooner during the grid traverse between opposite end points but still after the grid has reached a substantially constant velocity.

In yet another example, shown in FIG. 3(c), an exposure interval 50(c) is longer than the time for the grid to traverse between opposite endpoints and the value of $t_2$ is therefore selected to define source preparation interval 43(c). The dotted line 56, in FIG. 2, illustrates the grid motion for exposure intervals that exceed the time for the grid to traverse between opposite endpoints. In this example, the grid motion is reversed at its motion end point and continues until the exposure is complete. In FIG. 3(c) the duration of the exposure preparation interval 43(c) results in the exposure interval 50(c) taking place relative to the grid motion to minimize the number of grid pauses at the motion end points of the grid during the exposure interval. It should be appreciated that the value for interval 43(c) in example 3(c) could be shorter or longer providing the grid did not pass through more endpoints than minimally required during the exposure interval 50(c).

In the embodiments illustrated in FIGS. 2 and 3(a)-(c), at least one of the grid oscillation start point and the start of the exposure interval is functionally related to the input technique factors and variable as a function thereof relative to the start of the exposure sequence.

With reference to FIGS. 4(a)-(c) and continuing reference to FIG. 1, an alternate embodiment of the present invention is shown. Like the first embodiment, the exposure sequences illustrated in FIGS. 4(a), (b) or (c) are comprised of an exposure preparation interval 60(a), (b) or (c) and an exposure interval 62(a), (b) or (c). In this embodiment, however, the exposure preparation interval 60(a), (b) or (c) and the radiation source preparation interval are the same duration. The grid acceleration commences at points 64(a), (b) or (c) respectively during the respective radiation source preparation interval. By commencing the grid motion during the radiation source preparation interval the exposure sequence can take place in the shortest possible time while avoiding the formation of grid lines on the image producing element. In this embodiment, $t_1$ is equal to the interval from the exposure sequence start (point 66(a), (b) or (c))

to the start of grid acceleration (point 64(a), (b) or (c)) and $t_2$ is equal to the interval from the exposure sequence start (point 66(a), (b) or (c)) to the start of the exposure interval (point 68(a), (b) or (c)). The value of $t_1$ is selected such that the grid acceleration commences during the exposure preparation interval 60(a), (b) or (c) at a point sufficient to allow for the grid to move from an at rest position at one of its end-points to a substantially constant velocity during the source preparation interval 60(a), (b) or (c).

As with the first embodiment, the LUT stores a plurality of timing information corresponding to a plurality of $t_1$ and $t_2$ values. Operator selection of exposure parameters causes the LUT to be addressed at locations where there is stored $t_1$ and $t_2$ values which establishes the relationship between the start and duration of interval 60(a), (b) or (c), the start of grid acceleration at point 64,(a), (b) or (c) ($t_0$ $_{grid\ acceleration}$) and the start of the exposure interval at point 68(a), (b) or (c) ($t_0$ $_{exposure\ interval}$).

In this alternate embodiment, the radiation source preparation time interval 60(a), (b) or (c) commences upon activation of the exposure sequence start means 28 at point 66(a), (b) or (c) ($t_0$ $_{exposure\ sequence}$) and is complete at point 68(a), (b) or (c) after a predetermined time ($t_2$) sufficient to prepare the x-ray source for radiation production. During the radiation source preparation interval the grid acceleration commences at point 64(a), (b) or (c) during the respective exposure preparation interval 60(a), (b) or (c) to allow the grid to accelerate from an at rest position at one of the end points to a substantially constant velocity before the exposure interval commences. After such time that the tube is prepared to produce radiation and the grid has reached a substantially constant velocity, exposure interval 62(a), (b) or (c) commences. The duration of the exposure interval 62(a), (b) or (c) is determined by the nature of the exposure parameters selected by the operator at operator interface 32 and dictates the point in time that grid acceleration commences to assure optimum grid motion in relation to exposure time.

Referring to FIG. 4(a), an exemplary exposure sequence is illustrated wherein the exposure interval is shorter than the time for the grid to traverse between opposite endpoints. The exposure sequence is initiated by the operator via exposure sequence start means 28 at point 66(a). The exposure sequence is comprised of a radiation source preparation interval 60(a) commencing at point 66(a) followed by an exposure interval 62(a) commencing at point 68(a). Specifically, in response to entry of exposure parameters on the operator interface 32, the controller selects a value of $t_2$ which defines interval 60(a). The controller also selects a value of $t_1$ which defines the grid acceleration start point. At the conclusion of the radiation source preparation interval ($t_2$), at point 68(a), the exposure interval 62(a) commences. At the expiration of the exposure interval 62(a) the controller terminates the exposure and signals the grid oscillation means 20 to set the grid adjacent a motion end point in preparation for the next exposure sequence.

In the example of FIG. 4(a) the grid acceleration start point is chosen via $t_1$ such that the exposure interval 62(a) begins and ends around the mid-point of the grid excursion between end points (44, 45). It is to be appreciated however, that beginning and ending the exposure interval around the midpoint of the grid excursion is not necessary to the practice of the invention.

In another example, shown in FIG. 4(b), the exposure interval 62(b) is shorter than the time for the grid to traverse between opposite end points and substantially longer than corresponding exposure interval 62(a) in FIG. 4(a). In this example the start of the grid acceleration at point 64(b) is selected such that the exposure interval 62(b) begins and ends approximately around the midpoint of the grid excursion between end points. In the example of FIG. 4(b) the value of $t_1$ is longer than the corresponding value of $t_1$ in FIG. 4(a) to permit the exposure interval 62(b) to occur around the midpoint of grid excursion and while the grid is traversing between opposite endpoints.

FIG. 4(c) illustrates grid motion for exposure intervals that exceed the time for the grid to traverse between endpoints. In the example shown in FIG. 4(c), the grid reaches a motion end point during the exposure interval and the controller causes grid motion to reverse and continue until the exposure is complete. The length of the exposure interval 62(c) results in the selection of a $t_1$ value that minimizes the number of grid pauses that occurs during the exposure interval. In FIG. 4(c) the value of $t_1$ was longer than illustrated in FIGS. 4(a) and (b). Alternatively, however, the value of $t_1$ could have been selected to be different value providing the grid did not pass through more endpoints than minimally required during the exposure interval 62(c).

In the embodiments illustrated in FIGS. 4(a)–(c), the same value, $t_2$, for the radiation preparation time interval was illustrated however, it should be appreciated that $t_2$ may vary as required for different exposure parameters selected by the operator or the type of x-ray tubes used.

In the embodiments illustrated in FIGS. 4(a)–(c), the grid oscillation starts during the radiation source preparation interval at a point relative to the start of the exposure preparation interval and as a function of the exposure interval to minimize the formation of grid lines on the image producing element. However, it should be appreciated that the grid acceleration can start before the start of the radiation source preparation interval as necessary to assure optimum grid motion in relation to exposure time.

In the above described embodiments the exposure interval is determined by the operator entry of technique factors into the operator interface terminal. However, many radiation imaging systems utilize an AEC to terminate the exposure when the film has been sufficiently exposed. Accordingly, the exposure interval is not known in advance thereof. However, in such systems, the values of $t_1$ and $t_2$ are used in one of the manners previously described.

In an alternate embodiment of the above imaging system, the controller 26 senses the activation of the exposure sequence start means 20 and signals the radiation source 4 to prepare for radiation production in response. Once the radiation source is ready to produce radiation it signals the controller with a radiation source ready signal. When the controller receives the radiation source ready signal the controller signals the grid oscillation means to commence oscillating the grid assembly starting from a position adjacent one of its motion endpoints. Shortly after signaling the grid oscillation means to commence oscillating the grid the controller signals the generator to commence the exposure interval. If the system has an AEC, the exposure interval is terminated when the AEC detects a predetermined amount of radiation otherwise, the controller terminates the exposure interval after a predetermined amount of time. Upon termination of the exposure interval the radiation source signals the controller that the exposure is complete. In response to the exposure complete signal, the controller signals the grid oscillation means to set the grid adjacent a motion end point in preparation for the next exposure sequence. It should be appreciated that different grid characteristics, e.g., mass, will require adjustment of the time when the exposure interval commences.

Figure 4:
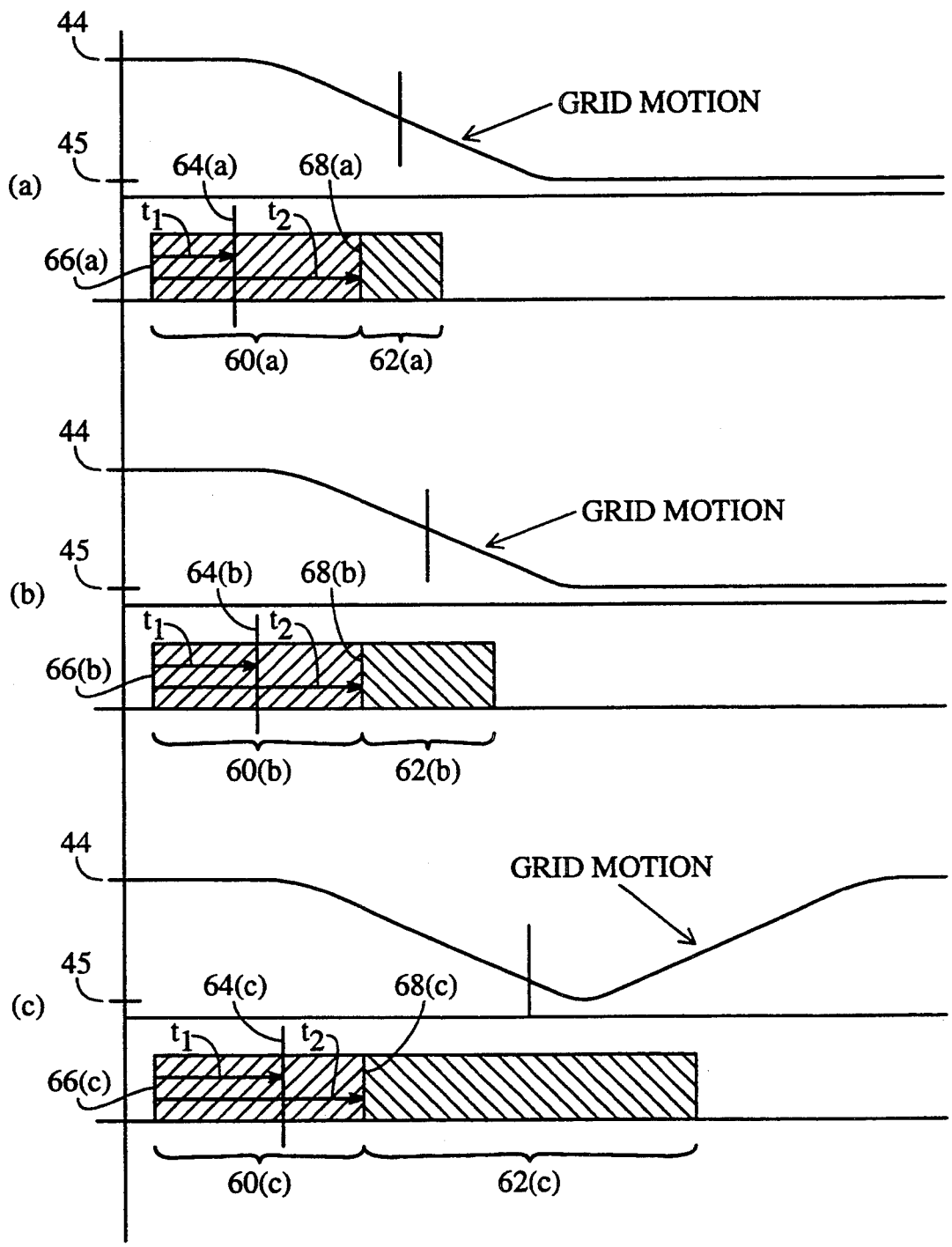
FIGS. 4(a)–(c) are exemplary graphical Illustrations of grid position versus time and exemplary exposure sequence timing relationships relative to said grid position versus time for various exposure sequence series according to an alternate embodiment of the invention.
Figure 5:
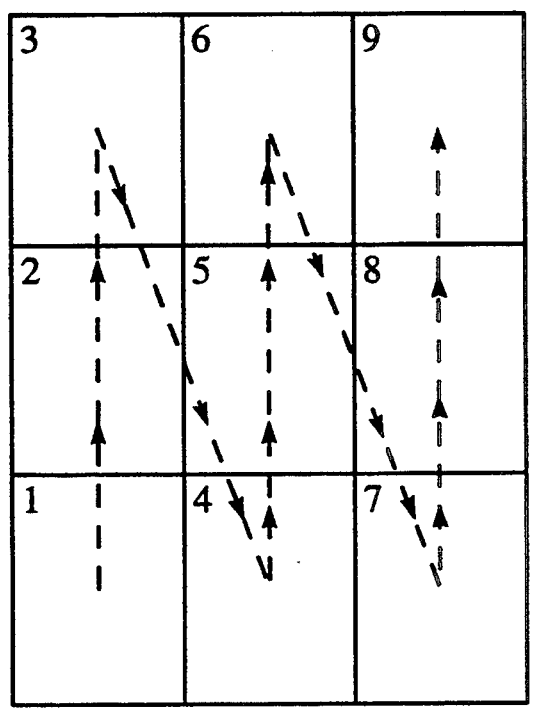
FIG. 5 is an Illustration of an exemplary exposure sequence series on a vertically oriented film cassette.
Figure 6:
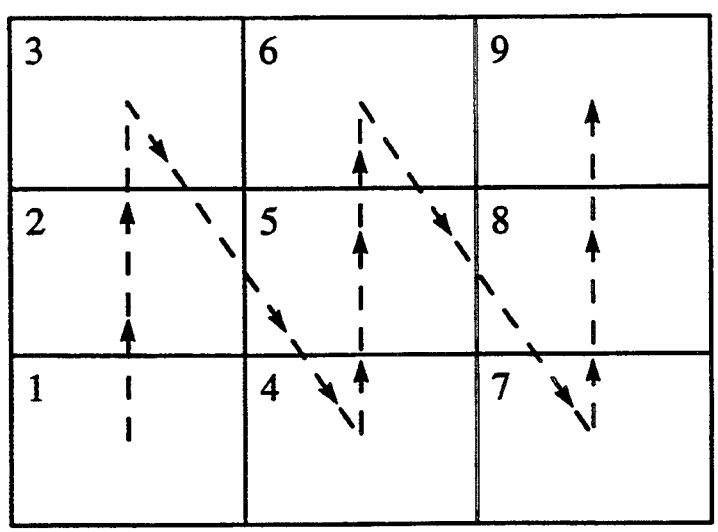
FIG. 6 is an illustration of an exemplary exposure sequence series on a horizontally oriented film cassette.

Referring now to FIGS. 5 and 6, two examples of an exposure sequence series are shown. An exposure sequence series is comprised of a plurality of separate exposure intervals occurring on separate portions of the image producing element. In FIG. 4, an exemplary 10 inch by 12 inch cassette combination is positioned in a "vertical" orientation. Film exposures 1 through 9 are taken in the sequence shown by the dashed arrows. It should be appreciated that the distance, and therefore the time, to advance the cassette from position 3 to position 4 is longer than from position 1 to position 2 due to the distance of the excursion. In FIG. 5, the cassette is positioned in a "horizontal" orientation. In like manner, film exposures 1 through 9 are taken in sequence. Again, the distance, and therefore the time, to advance the cassette combination from position 3 to position 4 is longer than from position 1 to position 2. Moreover, the time to advance the cassette between positions 1 and 2 and positions 3 and 4 in FIG. 4 is longer than the time to advance the cassette between positions 1 and 2 and positions 3 and 4 in FIG. 5 respectively due to the orientation of the cassette. In performing such exposure series, it is necessary to account for the time for the cassette to advance to its next exposure position between the end of one exposure and the start of the next exposure in the series. The present invention is well suited to account for these differences by virtue of different values of $t_1$ and $t_2$ being stored and retrieved in accordance with the exposure parameters selected by the controller or entered by the operator for the type of exposure sequence desired.

Figure 7A:
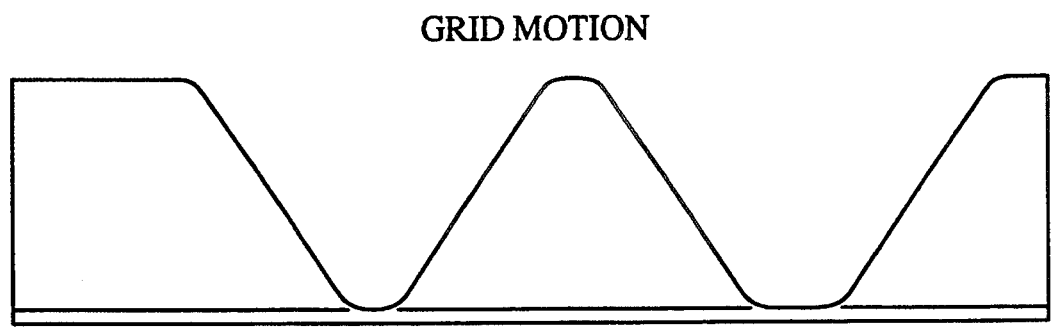
FIGS. 7(a)–(b) are exemplary graphical Illustrations of grid position versus time and an exemplary exposure sequence timing relationship relative to said grid position for a multiple exposure sequence.
Figure 7B:
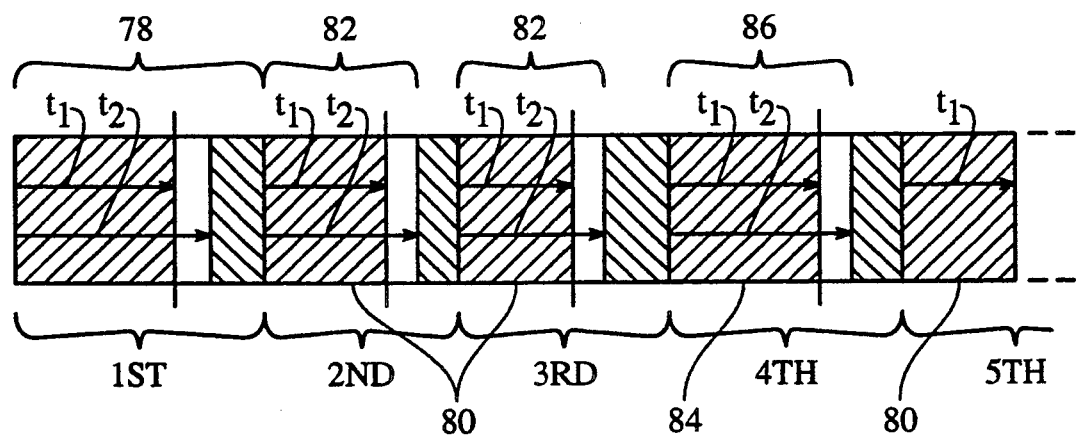

Referring now to FIGS. 7(a)–(b), the first exposure sequence of the series, e.g. position 1 on FIGS. 4 or 5, is conducted in one of the manners set forth above. After the first exposure 78 is complete, the x-ray tube anode is at exposure speed and the cathode filament is hot therefore, the exposure preparation interval does not require time to further prepare the x-ray tube. However, a time $t_1$ is required for the grid assembly to advance to a motion end point and the cassette to advance to another subsection of the image producing element after a previous exposure interval. intervals (80, 84) and (82, 86) correspond to the start of the grid acceleration and the start of the exposure interval respectively relative to the start of the corresponding exposure preparation interval.

As illustrated in FIGS. 7(a) and (b), intervals (80, 84) and (82, 86) for the second and subsequent sequence, commence at the end of the preceding exposure. Prior to the expiration of interval (80, 84) the grid assembly advances to a motion end point and the cassette advances to another exposure position. Generally, the time for the cassette to advance to another exposure position exceeds the time for the grid assembly to advance to a motion end point. At the expiration of the exposure preparation interval the grid acceleration commences. At the end of interval (82, 86) the exposure interval commences. This sequence repeats until the desired number of exposures have occurred.

As discussed above, the time for the cassette to move between positions 3 and 4 in FIGS. 4 and 5 is longer than the time for the cassette to move between position 1 and 2. If one value of $t_1$ is used for all exposures after the first exposure in the series the $t_1$ value must be of sufficiently duration that the cassette can advance between positions 3 and 4 (4th exposure), and 6 and 7 (7th exposure). Because the value of $t_1$ is longer in duration than the time required to advance the cassette between exposures 1 and 2, 2 and 3, 4 and 5, 5 and 6, 7 and 8, and 8 and 9 a corresponding delay results in these exposure sequence. Alternatively, as illustrated in FIG. 7(b), the controller retrieves and uses different values of $t_1$ or $t_2$ as required to maximize the system performance. For example, the controller retrieves first values of $t_1$ and $t_2$, intervals 80 and 82 respectively, to account for the cassette movement time between exposure positions 1 and 2, 2 and 3, 4 and 5, 5 and 6, 7 and 8, and 8 and 9 and retrieves second values of $t_1$ and $t_2$, intervals 84 and 86 respectively, from the LUT to account for the cassette movement time between exposure positions 3 and 4, and 6 and 7. This selective use of different $t_1$ and $t_2$ values maximizes the system exposure speed.

In an alternate embodiment, a cassette position sensor 18a is operatively connected to the cassette movement means and the controller to provide an indication to the controller that the cassette has arrived at the next exposure position. Since the grid assembly is generally capable of locating adjacent a motion end point much quicker than the cassette moves between exposure positions, the controller assumes that the grid assembly is adjacent a motion end point when the cassette position sensor indicates that the cassette is at the next exposure position. Accordingly, once the cassette is in position the controller signals the grid oscillation means to commence the grid oscillation. The controller commences the exposure interval shortly after signaling the grid oscillation means to commence oscillation.

If the system has an AEC, the exposure interval is terminated when the AEC detects a predetermined amount of radiation otherwise, the controller terminates the exposure interval after a predetermined amount of time. Upon termination of the exposure interval, the radiation source signals the controller that the exposure is complete. In response to the exposure complete signal, the controller signals the grid oscillation means to set the grid adjacent a motion end point and signals the cassette movement means to advance the cassette to the next exposure position. This sequence repeats until the desired number of exposures have occurred.

In the event there is uncertainty regarding whether the grid assembly locates adjacent a motion end point prior to the cassette arriving at an exposure position a grid position sensor 12a is provided to indicate to the controller when the grid is at a motion end point. The controller utilizes the grid position sensor 12a to hold off the commencement of the grid acceleration until the grid has arrived at a motion end point and the cassette is at the next exposure position.

In another embodiment of the present invention, the controller has a teach mode wherein the plurality of time-intervals, for both single exposures or exposure sequence series, are selectively altered by the controller after retrieval from the LUT. In the teach mode the controller learns the timing associated with the system operation and adjusts the time intervals accordingly to maximize the system operation.

In still another embodiment of the present invention, the operator selectively enters one or more of a plurality of time intervals corresponding to the various preparation times previously described. The entered values nullify any LUT time intervals retrieved by the controller and can represent unique system timing values selected by the operator. In this manner the operator can selectively modify the system operation to suit the requirements of a particular exposure sequence.

The above invention has been described with reference to the preferred embodiments. Obvious modifications, combinations of functions and alterations will occur to other upon reading the preceding detailed description. It is intended that the invention be construed as including all such modifications and alterations insofar as they come within the scope of the appended claims or the equivalents hereof.

Having described the preferred embodiment the invention is now claimed to be:

1. A radiographic diagnostic imaging system, comprising:
   a source of penetrative radiation for propagating a radiation beam along a path;
   an image producing element positioned in the beam path for receiving said radiation;
   a grid assembly positioned in the beam path between the radiation source and the image producing element, said grid assembly including a radiation absorbing grid strip;
   a grid assembly oscillation means for oscillating the grid assembly in direction transverse to the beam path;
   a controller for controlling the start of radiation production from the radiation source and for controlling the start of grid oscillation;
   an operator interface terminal connected to the controller for receiving operator input of technique factors and for communicating the same to the controller; and
   an exposure sequence start means for signalling the controller to start a first exposure sequence, said first exposure sequence comprised of:
      an exposure preparation interval comprising a radiation source preparation time interval and a grid oscillation start point; and
      an exposure interval;
   wherein at least one of said grid oscillation start point and the start of the exposure interval is functionally related to the input technique factors and variable as a function thereof relative to the start of the first exposure sequence.

2. The imaging system as set forth in claim 1 wherein the radiation source is comprised of a filament and an anode, and wherein the preparation interval is comprised of an interval of time sufficient for the filament of the radiation source to be heated by an electrical current to the point that electrons are boiled off and the anode of the radiation source is accelerated from an at rest position to a constant angular velocity.

3. The imaging system as set forth in claim 1 further including,
   a lookup table connected to the controller for storing data values comprised of at least one of a first time value corresponding to the time between the start of the exposure preparation interval and the grid oscillation start point and a second time value corresponding to the time between the start of the exposure preparation interval and the start of the exposure interval.

4. The imaging system as set forth in claim 3 wherein said values are selectively retrieved by the controller in response to operator input of technique factors, the controller operating the imaging system in response to at least one of the operator input technique factors and the retrieved data values.

5. The imaging system as set forth in claim 3 wherein the grid oscillation start point occurs at one of the end of the radiation source preparation time interval and during the radiation source preparation time interval.

6. The imaging system as set forth in claim 1 further including a cassette movement means for positioning select subsections of the image producing element in the beam path in response to signals from the controller.

7. The imaging system as set forth in claim 6 wherein the controller further synchronizes the movement of the cassette and the activation of the radiation source to produce a second exposure sequence on a select subsection of the image producing element, said second exposure sequence comprised of a second exposure preparation interval and a second exposure interval, said second exposure preparation interval providing sufficient time for the cassette to advance to a second exposure position and the grid to advance to a motion end point and commence oscillation therefrom, said radiation source commencing the second exposure interval at the end of the second exposure preparation interval.

8. The imaging system as set forth in claim 7 wherein at least one of the start of the grid oscillation and the start of the exposure interval for the second exposure sequence is functionally related to the input technique factors and variable as a function thereof relative to the start of the second exposure sequence.

9. The imaging system as set forth in claim 6 further including,
   an automatic exposure control means at least partially disposed in the radiation beam path for sensing the radiation in the beam path and for signaling at least one of the radiation source and the controller when a predetermined amount of radiation has been received by said exposure control means.

10. The imaging system as set forth in claim 9 wherein the controller further synchronizes the movement of the cassette and the activation of the radiation source to produce a second exposure sequence on a select subsection of the image producing element, said second exposure sequence comprised of a second exposure preparation interval and a second exposure interval, said cassette advancing to a second exposure position and said grid assembly advancing to a grid motion end point and commencing oscillating therefrom during the second exposure preparation interval, said radiation source commencing the production of radiation for the second exposure interval shortly after the commencement of the grid oscillation.

11. The imaging system as set forth in claim 9 further including at least one of a cassette position sensor operatively connected to the cassette and the controller for indicating to the controller that the cassette has arrived at an exposure position and a grid position sensor operatively connected to the grid assembly and the controller for indicating to the controller that the grid assembly has arrived at an end point of grid motion travel.

12. An apparatus for controlling an exposure sequence of a radiographic imaging system, said system including of a source of penetrative radiation for propagating a radiation beam along a path, a grid assembly having a radiation absorbing grid strip positioned in the beam path, a grid assembly oscillation means for oscillating the grid assembly in a direction transverse to the beam path and an exposure sequence start means, said apparatus comprising:

a controller for controlling the start of radiation production from the radiation source and for controlling the start of grid oscillation; and an operator interface terminal operatively connected to said controller for receiving operator input of technique factors and for communicating said input to the controller, wherein the exposure sequence start means signals the controller to start the exposure sequence, said sequence comprised of an exposure preparation interval including a radiation source preparation interval and a grid oscillation start point, and an exposure interval; wherein at least one of the grid oscillation start point and the start of radiation production is a function of said input technique factors relative to the start of the exposure sequence.

13. The apparatus as set forth in claim 12 further including, a memory means operatively connected to the controller for storing a first and second time value, said controller retrieving the first and second time values and controlling the the grid oscillation start point and the start of radiation production in relation to the first and second time values.

14. The apparatus as set forth in claim 12 further including, an automatic exposure control means operatively connected to the controller and comprising means for sensing radiation impinging thereon, said exposure control means generating an output signal to the controller when a select amount of radiation has been received by said radiation detection means, said controller terminating the exposure interval on receipt of said output signal.

15. The apparatus as set forth in claim 14 further including a cassette movement means operatively connected to the controller for synchronizing the movement of select portions of an image producing element into the beam path relative to the termination of a previous exposure sequence.

16. The apparatus as set forth in claim 15 wherein the controller further synchronizes the movement of the cassette movement means and the start of radiation production to produce a second exposure sequence on a select portion of the image producing element, said second exposure sequence comprised of a second exposure preparation interval and a second exposure interval, said cassette movement means advancing the cassette to a second exposure position and said grid assembly advancing to a grid motion end point and commencing oscillating therefrom during the second exposure preparation interval, said radiation source commencing the start of radiation production for the second exposure interval shortly after commencement of the grid oscillation.

17. A method of controlling the movement of a grid assembly in a diagnostic imaging system during an exposure sequence, the method comprising the steps of:

positioning the grid assembly and at least a portion of an image producing element in a radiation beam path produced by the diagnostic imaging system;

entering technique factors into an operator interface terminal;

activating an exposure sequence start means;

preparing a radiation source to produce a radiation beam;

accelerating the grid assembly from an at rest position to a substantially constant velocity;

causing the radiation source to produce radiation along the beam path;

exposing at least the portion of the image producing element to the radiation beam; and terminating the radiation produced by the radiation source;

wherein the commencement of at least one of the accelerating step and the exposing step is functionally related to the input technique factors and variable as a function thereof relative to the start of the exposure sequence.

18. The method as set forth in claim 17 wherein the accelerating step commences at one of the end of the preparing step and during the preparing step.

19. The method as set forth in claim 17 further including the step of setting the grid adjacent a grid motion end point after the terminating step.

20. The method as set forth in claim 19 comprising the further steps of, moving an unexposed portion of the image producing element Into the beam path;

accelerating the grid assembly from an at rest position to a substantially constant velocity;

causing the radiation source to produce radiation along the beam path;

exposing the unexposed portion of the Image producing element in the beam path to the radiation beam;

terminating the radiation produced by the radiation source;

setting the grid adjacent a grid motion end point; and repeating the above steps until all select subsections of the Image producing element are exposed.

* * * * *